United States Patent [19]

Trojanowski et al.

[11] Patent Number: 5,281,521
[45] Date of Patent: Jan. 25, 1994

[54] MODIFIED AVIDIN-BIOTIN TECHNIQUE

[75] Inventors: John Q. Trojanowski; Virginia M-Y. Lee, both of Philadelphia, Pa.

[73] Assignee: The Trustees of The University of Pennsylvania, Philadelphia, Pa.

[21] Appl. No.: 915,919

[22] Filed: Jul. 20, 1992

[51] Int. Cl.⁵ ............... G01N 33/532; G01N 33/577
[52] U.S. Cl. ............................ 435/7.5; 435/7.2; 435/7.92; 435/960; 435/962; 436/501; 436/548
[58] Field of Search ............... 435/7.5, 962, 960, 7.92, 435/7.2; 436/548, 501; 530/388.1

[56] References Cited

U.S. PATENT DOCUMENTS

| 4,481,298 | 11/1984 | Cone et al. | 436/500 |
| 5,122,453 | 6/1992 | Martin et al. | 435/7.24 |

OTHER PUBLICATIONS

Harlow & Lane (eds) in *Antibodies, a Laboratory Manual*, (1988) pp. 321-323, 390-400, 591-593, 632-633.
Arai, H., et al., *Proc. Natl. Acad. Sci. U.S.A.* 87, 2249 (1990).
Baetge E. E., et al., *Proc. Natl. Acad. Sci., U.S.A.*, 85:3648 (1988).
Foulds S., et al., *Hybridoma*, 9:91 (1988).
Friedman H. S., et al., *Med. J. Neuropathol. Exp. Neurol.*, 44:592 (1985).
Hammang J. P., et al., *Neuron*, 4:775 (1990).
Hsu S. M., et al., *Am. J. Pathol.*, 75:734 (1981).
Haspel M. V., et al., *Cancer Res.*, 45:3951 (1985).
Imam A., et al., *J. Immunol. Methods*, 86:17 (1986).
Johansson O., et al., *Neuroscience*, 6:1857 (1981).
Lee V. M.-Y., et al., *J. Neurosci.*, 7:3474 (1987).
Lee V. M.-Y., et al., *J. Neurochem.*, 42:25 (1984).
Long D. M., *J. Neurosurg.*, 32:127 (1970).
Molenaar W. M., et al., *Acta. Neuropathologica*, 83:46 (1991).
Moolenaar CECK, et al., *Cancer Res.*, 50:1102 (1990).
Nielsen B., et al., *Hybridoma*, 6:103 (1987).
Pleasure, S. J., et al., *Proc. Natl. Acad. Sci., U.S.A.*, 87:8496 (1990).
Schmidt, M. L., et al., *Am. J. Pathol.* 136, 1069 (1990).
Stern, R. A., et al., *Am. J. Pathol.*, 134, 973 (1989).
Stewart P. A., et al., *J. Neurosurg.*, 67:697 (1987).
Wilson, I. A., et al., "Structural Aspects of Antibodies and Antibody-Antigen Complexes," *Ciba Foundation Sym.*, 159:13 (1991).
Sternberger L. A., et al., *J. Histochem. Cytochem.*, 18:315 (1970).

*Primary Examiner*—David Saunders
*Attorney, Agent, or Firm*—Woodcock Washburn Kurtz Mackiewicz & Norris

[57] ABSTRACT

A method for preparing an antigen specific probe is provided by incubating a primary antigen specific monoclonal antibody with a biotinylated secondary antibody to produce a complex of the primary and secondary antibodies. The staining pattern produced by these probes reflects the specificity of the monoclonal antibody in the complex and the labeling of irrelevant, endogenous immunoglobulins is reduced substantially. This novel, indirect immunohistochemical method can be used to study normal and diseased tissues using a variety of monoclonal antibodies.

8 Claims, 4 Drawing Sheets

MODIFIED AVIDIN-BIOTIN TECHNIQUE

BACKGROUND OF THE INVENTION

In indirect enzyme-linked immunohistochemical procedures, the secondary antibody serves the pivotal role of linking the primary antibody bound to the antigen of interest in a tissue section with a tertiary complex containing an enzyme reporter molecule. Two of the most commonly applied methods are the peroxidase-antiperoxidase (PAP) (Sternberger L. A., et al., "The Unlabelled Antibody Enzyme Method of Immunohistochemistry: Preparation and Properties of Soluble Antigen-Antibody Complex (Horseradish-Antihorseradish Peroxidase) and its use in Identification of Spirochetes," J. Histochem. Cytochem., 18:315 (1970)) and the avidin-biotin-complex (ABC) method (Hsu S. M., et al., "A Comparative Study of Peroxidase-Antiperoxidase Method and an Avidin-Biotin Complex Method for Studying Polypeptide Hormones with Radioimmunoassay Antibodies," Am. J. Pathol., 75:734 (1981)). In the latter method, biotinylated secondary antibodies are applied to tissue sections in order to link peroxidase labeled avidin-biotin complexes with primary antibodies bound to a specific antigen in situ. Simplicity, high signal amplification and low background are features of the ABC method that have prompted its widespread use as an immunohistochemical detection system.

In the PAP, ABC and other indirect immunohistochemical methods, the secondary antibody used to recognize the primary antibody could bind to endogenous immunoglobulins in murine tissues. This source of nonspecific background can be eliminated from many normal tissues by in vivo perfusion with buffer to wash out the vascular compartment. However, perfusion with buffer may not wash out extravasated immunoglobulins, especially from diseased or lymphoid tissues. Thus, it would be attractive to devise an immunohistochemical method that removes the need to eliminate endogenous immunoglobulins. This would greatly facilitate efforts to study normal or diseased murine tissues and to characterize transgenic mouse models of a variety of diseases. For example, immunohistochemical studies of tumors and tumor xenografts in nude mice could be conducted using a wide variety of existing mouse monoclonal antibodies (mAb) if background staining due to the presence of endogenous mouse immunoglobulins could be eliminated in tissue sections.

Several strategies have been devised to overcome this problem. For example, an acidic-potassium permanganate solution (Johansson O., et al., "Immunohistochemical Support for Three Putative Transmitters in one Neuron: Coexistence of 5-Hydroxytryptamine Substance P- and Thyrotropin Releasing Hormone-like Immunoreactivity in Medullary Neurons Projecting to the Spinal Cord," Neuroscience, 6:1857 (1981)) has been used to remove immunoglobulins from tissue sections, but this procedure damages tissues and/or the antigens of interest. Alternatively, it is possible to biotinylate the mAbs of interest and detect them with a reporter molecule coupled to avidin (Baetge E. E., et al., "Transgenic Mice Express the Human Phenylethanolamine N-Methyltransferase Gene in Adrenal Medulla and Retina," Proc. Natl. Acad. Sci., USA, 85:3648 (1988); Haspel M. V., et al., "Generation of Tumor Cell-Reactive Human Monoclonal Antibodies using Peripheral Blood Lymphocytes from Actively Immunized Colo-Rectal Carcinoma Patients," Cancer Res., 45:3951 (1985); Imam A., et al., "A Novel Immunoperoxidase Procedure of using Human Monoclonal Antibodies for the Detection of Cellular Antigens in Tissue Sections," J. Immunol. Methods, 86:17 (19B6)). However, this strategy is impractical and costly when large panels of mAbs are used.

Another potential strategy would be to block access of the anti-mouse secondary antibodies to the endogenous mouse immunoglobulins by pre-incubating the tissue sections with a low dilution of Fab' fragments from an irrelevant species that recognize endogenous mouse immunoglobulins (Foulds S., et al., "The use of Fab' fragments in a screening method for the Detection of Human Monoclonal Antibodies," Hybridoma, 9:91 (1988); Nielsen B., et al., "A Method for the Blocking of Endogenous Immunoglobulin on Frozen Tissue Sections in the Screening of Human Hybridoma Antibody in Culture Supernatants," Hybridoma, 6:103 (1987)), but this approach requires large quantities of expensive Fab' fragments. Thus, there remains a need to improve the specificity and sensitivity of indirect immunohistochemical methods.

SUMMARY OF THE INVENTION

The present invention is directed to a method for preparing an antigen specific probe. The method involves incubating a selected primary antigen specific monoclonal antibody with a selected biotinylated secondary antibody to produce a complex of the primary and secondary antibodies. A selected volume of the primary antibody is incubated with an equal volume of secondary antibody and diluted normal mouse serum is added.

When mouse tissues are probed with murine monoclonal antibodies (mAbs) by indirect immunohistochemistry, the secondary antibody detects tissue-bound mAbs and irrelevant, endogenous mouse immunoglobulins. The latter are a source of confounding background, especially in disease tissues. To circumvent this problem, complexes of primary mAbs and biotinylated secondary antibodies were generated in vitro for use as antigen specific probes. After blocking free binding sites in the complexed secondary antibodies with normal mouse serum, the complexes were applied to mouse tissue sections, and tissue-bound complexes were visualized with an avidin-biotin detection system. Complexes formed with 12 different rat or mouse mAbs were used to probe sections of normal mice, tumor bearing transgenic mice and mice with tumor xenografts. The staining patterns produced by these probes reflected the specificity of the mAbs in the complexes, and the labeling of irrelevant, endogenous mouse immunoglobulins was reduced substantially. This novel, indirect immunohistochemical method can be exploited to study normal and diseased mouse tissues using a variety of murine mAbs.

DESCRIPTION OF THE DRAWINGS

FIG. 2 shows tumor tissues stained by the standard ABC method (left hand column) and the method of the invention (right hand column). FIGS. 2A to 2D show the same retinoblastoma stained with FNP7. Note the significant reduction in background staining and better delineation of the positive. cells using the method of the invention (arrows in FIGS. 2B and 2D), but not the standard ABC method (arrows in FIGS. 2A and 2C).

FIG. 3 shows tumor tissues stained with different mAbs using the invention.

FIG. 4 shows sections of normal mouse (FIGS. 4A to 4D) and human (FIGS. 4E to 4H) cerebellum were stained with the standard ABC method (FIGS. 4A, 4C, 4E, 4G) and the method of the invention (FIGS. 4B, 4D, 4F, 4H). A and B were stained with SY38, while FIGS. 4C and 4D were probed with RM093. The results in FIGS. 4A and 4B are the same, but note reduced axonal staining by RM093 using the invention (arrow head in FIG. 2D) compared to the standard method (arrow head FIG. 2C). FIGS. 4E and 4F were stained with MOC-1, while FIGS. 4G and 4H were stained with anti-MBP. The results in FIGS. 4E and 4F are the same, but MBP staining is less intense using the method of the invention. This is evident in the granular cell layer (arrow in FIGS. 4G and 4H) and near Purkinje cells (arrow head in 4G and 4H) (M: molecular layer; G: granular layer; W: white matter) (Bar=10 μm)

DETAILED DESCRIPTION OF THE INVENTION

In the present invention, a novel modification of the Avidin-Biotin Complex (ABC) method is provided. This method was used to study diseased and normal mouse tissues with rat and mouse mAbs. In this novel procedure, all the immunoglobulin binding sites in the biotinylated secondary antibody were occupied either by the mAbs or by immunoglobulins in normal preimmune mouse serum. A variety of mouse and rat mAbs were used to probe tissue sections from tumor bearing transgenic mice, normal mouse brains, and nude mouse brains with tumor xenografts to evaluate the method of the present invention. Also, sections of normal human cerebellum were studied. These results were compared with those obtained using a standard ABC method. The method of the present invention was found to be superior to the conventional ABC method because it detected a wide variety of antigens in normal and diseased mouse tissues using rat and mouse mAbs, and because it substantially reduced staining of the endogenous mouse immunoglobulins present in mouse tissue samples. This method facilitates immunohistochemical studies of normal, diseased and transgenic tissues.

The present invention comprises the preparation of an antigen specific probe via incubation of a selected primary antigen specific monoclonal antibody with a selected secondary antibody to produce a complex of the primary and secondary antibodies. The method includes incubating the primary antibody and secondary antibody in equal selected volumes and adding diluted normal mouse serum. The final concentration may be in the range of from about 1:1200 to about 1:3200, preferably 1:2400. The incubation step may be performed at a temperature in the range of from about 35° C. to about 39° C, and for up to 60 minutes, preferably at 37° C. for one hour.

The primary antigen specific monoclonal antibody is selected from the group consisting of MOC-1, DP1, RMd020, H014, RM0254, FNP7, SY38, 2.2B10, NR4, RM093, RM055 and anti-MBP. The secondary antibody may be any biotinylated antibody that recognizes the primary antibody, preferably selected from the group consisting of biotinylated anti-mouse, biotinylated anti-rat or biotinylated anti-rabbit antibodies.

The primary antibody - biotinylated secondary antibody complex may be carried in a diluent of 1% fetal calf serum in 0.1M Tris buffer, pH 7.6. The complex of primary and secondary antibodies may be chilled at temperatures of from about 2° C. to about 6° C., preferably 4° C., for at least 30 minutes before applying to tissue sections.

An antibody is said to be "specifically reactive" with a molecule if it is capable of binding with the molecule to thereby couple the molecule to the antibody. The term "epitope" is meant to refer to that portion of a hapten which can be recognized and bound by an antibody. An antigen may have one or more than one epitope. An "antigen" is capable of inducing an animal to produce antibody capable of binding to an epitope of that antigen. The specific reaction referred to above is meant to indicate that the antigen will immunoreact, in a highly selective manner, with its corresponding antibody and not with the multitude of other antibodies which may be evoked by other antigens.

The term "antibody" (Ab) or "monoclonal antibody" (Mab) as used herein is meant to include intact molecules as well as fragments thereof (such as, for example, Fab and F(ab')$_2$ fragments) which are capable of binding an antigen. Fab and F(ab'$_2$) fragments lack the Fc fragment of intact antibody, clear more rapidly from the circulation, and may have less non-specific tissue binding of an antibody.

The antibodies of the present invention may be prepared by any of a variety of methods, for example as described in Arai, H., et al., "Defined Neurofilament, τ, and β-Amyloid Precursor Protein Epitopes Distinguish Alzheimer from Non-Alzheimer Senile Plaques," *Proc. Natl. Acad. Sci. U.S.A.* 87, 2249 (1990); Schmidt, M. L., et al., "Relative Abundance of Tau and Neurofilament Epitopes in Hippocampal Neurofibrillary Tangles," *Am. J. Pathol.* 136, 1069 (1990); and Stern, R. A., et al., "Monoclonal Antibodies to a Synthetic Peptide Homologous with the First 28 Amino Acids," *Am. J. Pathol.*, 134, 973 (1989). Methods for the production of such antibodies are well known and described fully in the literature. See e.g., Sambrook et al., "Molecular Cloning: A Laboratory Manual", second edition, Cold Spring Harbor Press, Vol. 3, Ch. 18 (1989). For example, the peptide or cells expressing the peptide, can be administered to an animal in order to induce the production of sera containing polyclonal antibodies that are capable of binding the peptide.

Monoclonal antibodies can be prepared using known hybridoma technology. In general, such procedures involve immunizing an animal with a peptide antigen. The splenocytes of such animals are extracted and fused with a suitable myeloma cell line. Any suitable myeloma cell line may be employed in accordance with the present invention. After fusion, the resulting hybridoma cells are selectively maintained in a suitable medium and then cloned by limiting dilution. The hybridoma cells obtained through such a selection are then assayed to identify clones which secrete antibodies capable of binding the peptide of the invention.

The antibodies can be detectably labeled as is known in the art. Immunohistochemical techniques such as immunoblotting or Western blotting are included within the scope of the invention.

Generally, conventional immunohistochemistry involves staining cryosectioned tissue samples with primary antibody, followed by contact with secondary antibody, such as a biotinylated antibody. The tissue is then incubated in avidin-conjugated horseradish peroxidase macromolecular complex followed by chromagen incubation. Fluorescein may then be added to observe the epitope pattern.

Immunoblotting may involve the analysis of protein on sodium dodecylsulfate-polyacrylamide gel electrophoresis SDS-PAGE. The gel may be run under nonreducing conditions and the samples transferred to a membrane, nitrocellulose for example. The membrane is incubated in primary antibody-containing media. The filter is developed using a secondary antibody, such as an alkaline phosphatase-conjugated antibody.

The method described here is dependent on the effective blocking of the unoccupied binding sites in the biotinylated antibody with normal mouse serum after the biotinylated antibody forms a complex with the primary antibody in vitro. During the initial stages in optimizing this important blocking step, a range of dilutions of the mouse serum (i.e., from 1:40 to 1:9600) were studied, and it was determined that concentration ranges of 1:1200 to 1:3200 dilutions were effective, and a 1:2400 dilution was most effective in preventing the complexed biotinylated secondary antibody from binding to endogenous mouse immunoglobulins in the tissue sections. This dilution blocked effectively when a range of concentrations of the biotinylated antibody was complexed with a given mAb.

To evaluate the method of the invention, several mAbs of different isotypes (IgM, IgG$_1$, IgG$_{2a}$) were used to stain tissue sections. This method was also tested with antigens located within different compartments of neurons or glia, i.e., cytoplasmic intermediate filaments (e.g., neurofilament, NF, proteins and glial fibrillary acidic protein, GFAP), cytoplasmic vesicles (i.e., synaptophysin), and plasma membrane (N-CAM). Normal tissue and tissue infiltrated with tumor cells were also used to test this method. The optimal dilutions shown in Table 1 were obtained by empirical titration.

Invasive tumors, spontaneous or xenografts, may disrupt capillary structure leading to edema and accumulation of endogenous immunoglobulin around and within the affected tissues (Long D. M., "Capillary Ultrastructure and the Blood-Brain Barrier in Human Malignant Brain Tumors," *J. Neurosurg.*, 32:127 (1970); Stewart P. A., et al., "Quantitative Study of Microvessel Ultrastructure in Human Peritumoral Brain Tissue: Evidence for a Blood-Brain Barrier Defect," *J. Neurosurg.*, 67:697 (1987)). Thus, to test the ability of the invention to abolish the background staining due to endogenous immunoglobulin, sections of tissue infiltrated by tumors were stained in accordance with the teachings of the invention for comparison with the standard ABC method. Background due to endogenous mouse immunoglobulin was abolished almost completely (FIG. 2, B, D, F, and H) using the method of the invention. This procedure always yielded far less background than the standard ABC method (FIG. 2, A, C, E, and G).

Figure 2A:
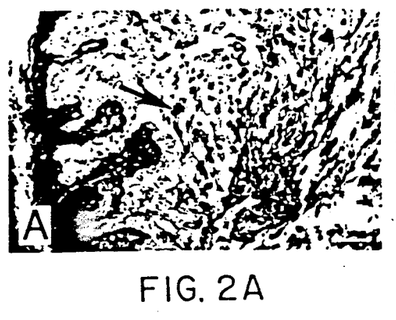
Figure 2B:
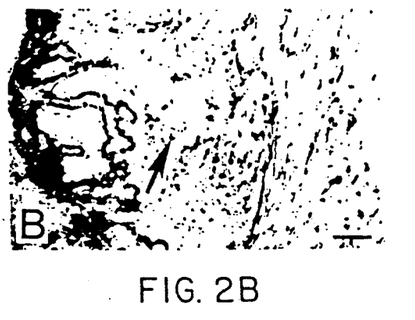
Figure 2C:
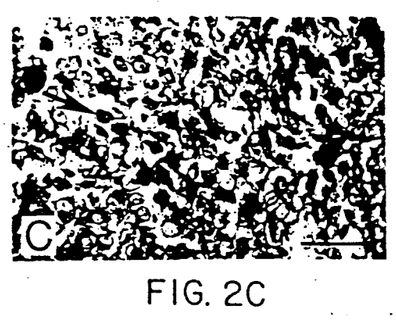
Figure 2D:
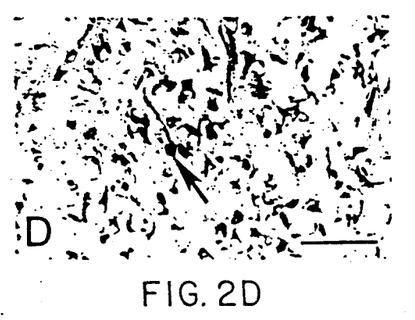

For example, when sections of an ocular transgenic mouse retinoblastoma were stained with both the standard and invention methods (FIG. 2, A to D), the latter procedure yielded more distinct signal for NF proteins (using FNP7) than the former method (compare FIG. 2A and 2C with 2B and 2D). This appeared to be due to the prohibition of labeling the extravasated mouse immunoglobulins in these ocular tumors by complexes used in the method of the invention.

Figure 2E:
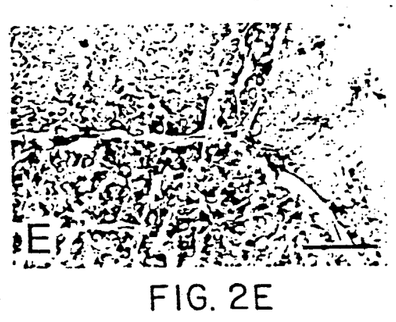
FIGS. 2E and 2F show a pheochromocytoma stained with RMd020. Note that the positively stained cells are better distinguished (compare lower half of FIGS. 2E and 2F) with the method of the invention.
Figure 2F:
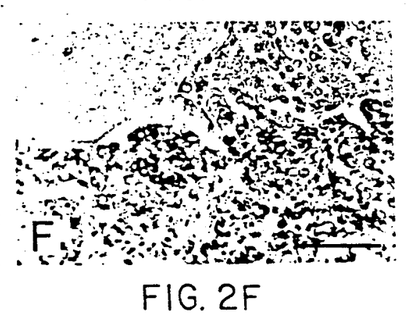
Figure 2G:
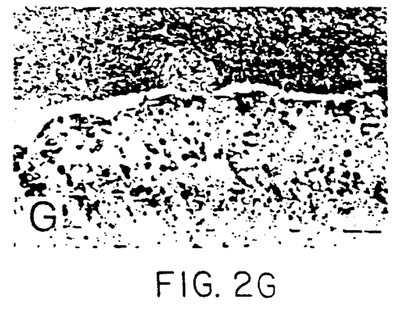
FIGS. 2G and 2H show the human tumor xenograft stained with H014. Note the reduced background staining in the surrounding brain tissue (compare upper portion of FIGS. 2G and 2H) with the method of the invention. (Bar=10 μm)
Figure 2H:
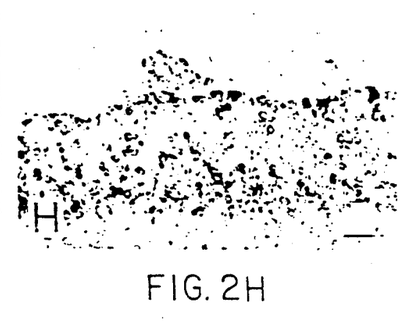
Figure 3A:
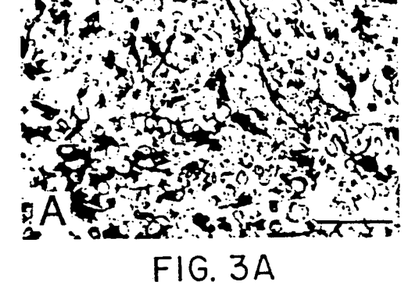
FIGS. 3A to 3C illustrate sections of mouse retinoblastoma stained with RM055, SY38, and DP1, respectively. The residual pigmented (P in FIGS. 3B and 3C) epithelium was not labelled by these mAbs, but the compressed retina (R in FIG. 3B) was SY38 positive and residual retinal fibers were NF positive (arrow in FIG. 3C).
Figure 3B:
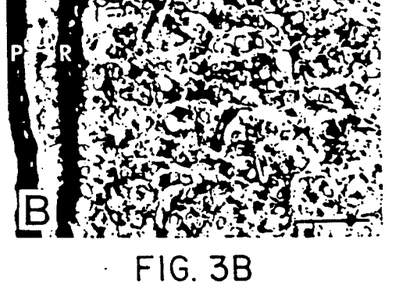
Figure 3C:
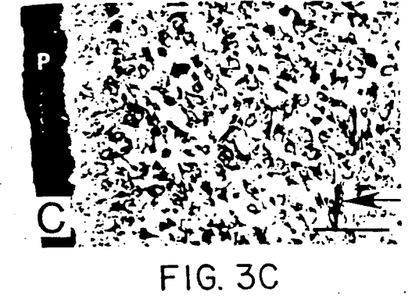
Figure 3D:
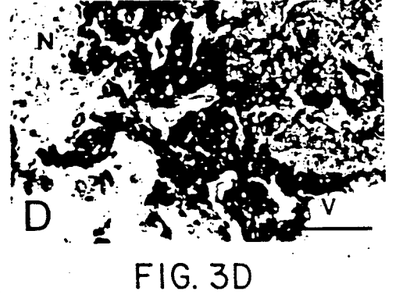
FIGS. 3D and 3E show a mouse pheochromocytoma stained with DP1 and SY38, respectively. Note the negative (N) cells and unstained blood vessel (V) in FIG. 3D. F shows the human tumor xenograft. A group of tumor cells stained with NR4 (arrow head) are positive. (Bar=10 μm)
Figure 3E:
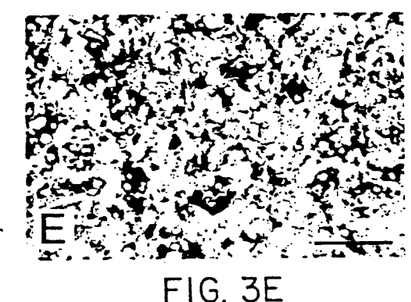
Figure 3F:
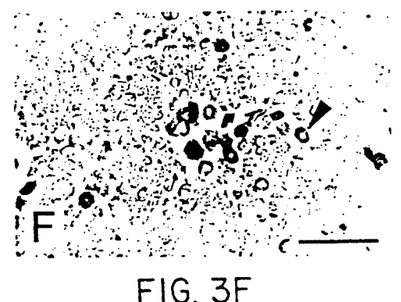
Figure 4A:
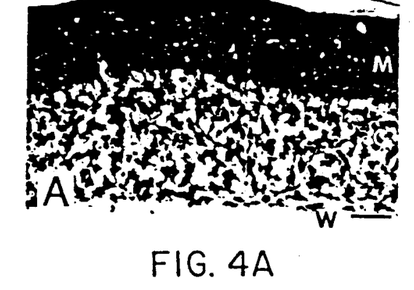
Figure 4B:
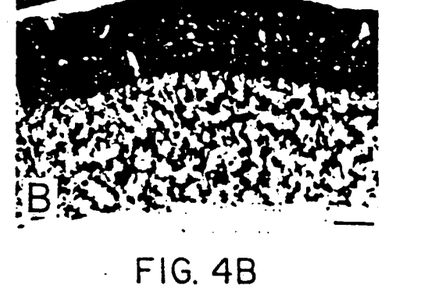
Figure 4C:
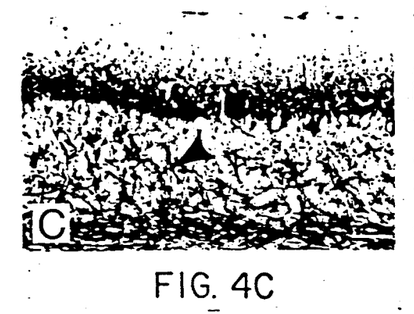
Figure 4D:
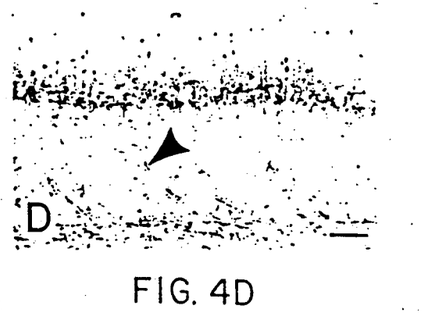
Figure 4E:
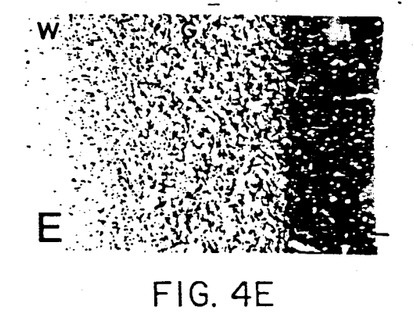
Figure 4F:
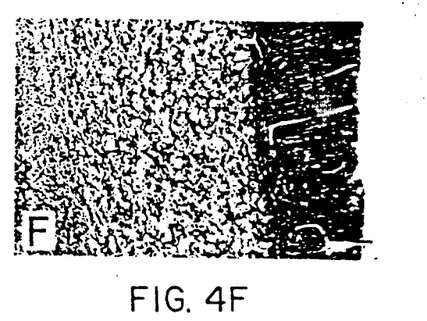
Figure 4G:
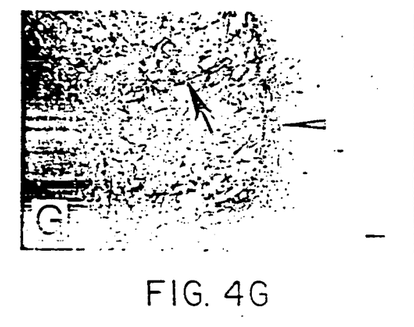
Figure 4H:
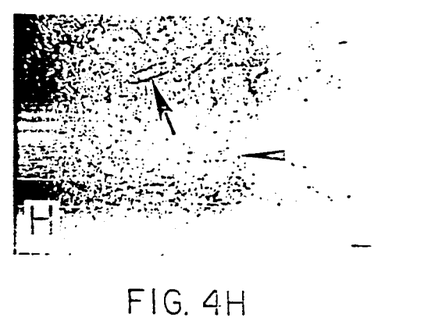

A similar reduction in background was achieved with the invention when it was used to probe an adrenal pheochromocytoma that developed in the same transgenic mouse (compare FIG. 2E with 2F). The NF positive neoplastic chromaffin cells were more sharply delineated with the modified ABC method. The same was true for the D283 MED-NGFR medulloblastoma cells xenografts stained with H014 in the nude mouse brains (compare FIG. 2G and 2H).

Improved staining results were demonstrated with the method of the invention when mouse tumor tissues were probed with different mAbs (FIG. 3). Specifically, strong positive staining and minimal background were achieved in the retinoblastoma with RM055, SY38, DP1 (FIG. 3, A to C), RM0254 and RM093. Strong specific staining also was achieved in the pheochromocytoma stained with DP1, SY38 (FIG. 3, D and E), RM055, RM0254 and RM093. Tumor cells positive for NR4 were also identified by the modified method in the MED 283-NGFR xenograft in nude mice (FIG. 3, F).

Normal Mouse Cerebellum and Human Cerebellum

To evaluate further the relative sensitivity of the invention and standard ABC methods, normal mouse cerebellum and normal human cerebellum were stained by both methods using 12 different mAbs of diverse isotypes. The optimal staining dilutions of those mAbs were used, and the slides were developed in diaminobenzidine tetrahydrochloride solution. The mAbs can be separated into two major groups. Group 1 mAbs demonstrated equal staining sensitivity with either method. Group 2 mAbs demonstrated decreased staining sensitivity when the results obtained by the method of the invention were compared to the standard method. (Table 1)

Of the 10 mAbs that recognized mouse antigens, 4 of them (i.e., DP1, RMd020, FNP7, and SY38) exhibited a sensitivity comparable to the standard ABC method (FIG. 4, A and B). Six of them (i.e., RM0254, 2.2B10, NR4, RM055, RM093, and anti-MBP) showed a slight to moderate decrease in sensitivity when compared to the standard method (FIG. 4, C and D).

Antibodies were also tested with human cerebellum. Of the 11 mAbs that recognized human antigens, 7 of them (i.e., MOC-1, DP1, RMd020, H014, RM0254, FNP7 and SY38) demonstrated sensitivity comparable to that of the standard method (FIG. 4, E and F). Four of them (i.e., 2.2B10, NR4, RM055, and Anti-MBP) showed a slight to moderate decrease in sensitivity when the results obtained by the method of the invention were compared with the standard method (FIG. 4, G and H).

Preparation Of Antibody Complexes In Vitro

Figure 1:
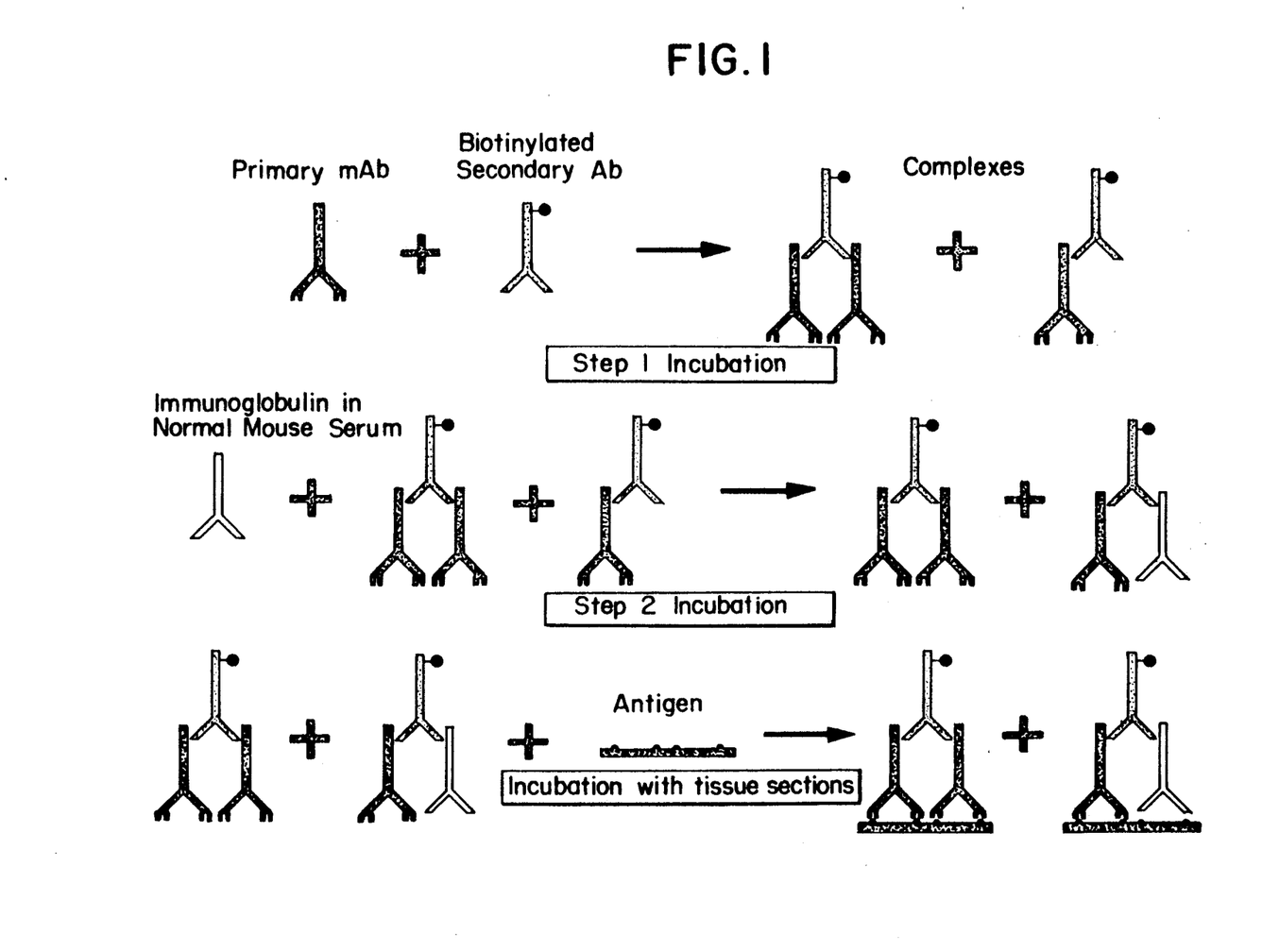
FIG. 1 is a diagrammatic summary of the modified ABC method as described in the text.

The principle innovation in this modified ABC method was the preparation of an antigen specific probe comprised of antibody complexes as shown in FIG. 1. These probes were prepared by incubating the primary mAb (i.e., the antigen specific mAb) and the "linking" or biotinylated secondary antibody with each other in vitro. This incubation step resulted in complexes of mAbs with the biotinylated secondary antibodies that recognized both mouse and rat mAbs. The process required two incubation steps, both of which led to a progressive dilution of the primary and secondary antibodies (FIG. 1). For this reason, the dilutions of the primary and secondary antibodies, or the concentration of a mAb in the complexes used as antigen specific probes in this modified ABC method refer to those achieved after this 2 step process (see Table 1).

quantitative studies of the modified and standard ABC methods using known concentrations of IgG, 2 different mAbs (i.e., FNP7 and RM093) were purified from ascites fluid to yield immunoglobulin concentrations of 798.4 and 296.2 $\mu$g/ml respectively, as described above. The optimal dilutions of the other antibodies were determined by empirical titration.

The second incubation step in the preparation of the antibody complex probe was designed to block the unoccupied binding sites on the secondary antibodies (FIG. 1). This step entailed the addition of a given volume of normal mouse serum (Sigma, St. Louis, MO) diluted in 1% FCS in 0.1M TRIS buffer to the solution containing the complexes formed by primary and secondary antibodies. Since preliminary studies indicated that a final dilution of 1:2400 of the normal mouse serum blocked binding of the complex to endogenous mouse immunoglobulin, the amount of mouse serum added was adjusted to achieve this final dilution. This solution was then placed in an incubator for 1 hour at 37° C.,

TABLE 1

MONOCLONAL ANTIBODIES USED IN THIS STUDY

| | | | | OPTIMAL WORKING DILUTIONS | | | |
|---|---|---|---|---|---|---|---|
| | | | | MOUSE TISSUE | | HUMAN TISSUE | |
| ANTIBODY | SPECIFICITY | PHOSPHORYLATION | ISOTYPE | MODIFIED METHOD | STANDARD METHOD | MODIFIED METHOD | STANDARD METHOD |
| GROUP 1: mAbs with equal staining sensitivity with either method | | | | | | | |
| MOC-1[a] | N-CAM | NA | IgG$_1$ | a | a | 12–36[c] | 100–36 |
| DP1 | NF-H | – | IgG$_{2a}$ | 3–36 | 3–36 | 3–36 | 3–36 |
| RMdO20 | NF-H | – | IgG$_1$ | 3–36 | 3–36 | 96–36 | 3–36 |
| HO14[a] | NF-M | +++ | IgG$_{2a}$ | a | a | 3–36 | 3–36 |
| RMO254[e] | NF-M | ind. | IgM | 3–36[e] | 3–36[e] | 96–36[e] | 96–36[e] |
| FNP7 | NF-M | – | IgG$_1$ | 1.61 $\mu$g/ml-36[d] | 0.773 $\mu$g/ml-36 | 1.61 $\mu$g/ml-36 | 0.048 $\mu$g/ml-36 |
| SY38 | Synaptophysin | NA | IgG$_1$ | 15–36 | 90–36 | 15–36 | 90–36 |
| GROUP 2: mAbs with staining sensitivity higher in the standard method than the modified method | | | | | | | |
| 2.2B10 | GFAP | NA | IgG$_{2a}$ | 150–36 | 300–36 | 150–36 | 300–36 |
| NR4 | NF-L | ind. | IgG$_1$ | 3–24 | 3–36 | 3–24 | 3–36 |
| RMO93[b] | NF-M | + | IgG$_1$ | 4.38 $\mu$g/ml-36 | 0.9625 $\mu$g/ml-36 | b | b |
| RMO55 | NF-M | ++ | IgG$_1$ | 9–36 | 36–36 | 18–36 | 36–36 |
| anti-MBP | Myelin basic protein | NA | ND | 3–24 | 6–36 | 3–24 | 6–36 |

[a]These mAbs recognize human but not mouse NF-M
[b]These mAbs recognize mouse but not human antigens
[c]The first number specifies the working dilution of the primary mAb, the second number denotes the working dilution of the secondary antibody and the ABC complex. (e.g., 3–36 denotes 1:3 dilution of the primary antibody and 1:36 dilution of the secondary antibody and the streptavidin-biotin-complex)
[d]Refers to the concentration of these mAbs in mg/ml, the second digit refers to the dilution of the secondary antibody
[e]RMO254 has equal sensitivity with either method when staining human tissue but reduced sensitivity in the modified ABC method when staining mouse tissue sections ABBREVIATIONS:
ind. = phosphorylation independent epitope
–, ++, +++ = poorly moderately, heavily phosphorylated epitope, respectively
NF-L, NF-M, and NF-H = low, medium and high molecular weight NF proteins, respectively
ND = not determined
NA = not applicable In the first incubation step, a given volume of the mAb was incubated with an equal volume of the diluted stock solution of the biotinylated secondary antibodies (Supersensitive Kit, BioGenex, San Ramon, CA) at 37° C. for 1 hour in an EPPENDORF test tube. As recommended by the vendor, the stock solution of the biotinylated secondary antibody was used in this first step at dilutions that ranged from 1:10 to 1:100. The working dilution of the primary antibody and the dilution of the biotinylated secondary antibody are listed in Table 1. The diluent for the primary antibodies, secondary antibodies, and streptavidin-biotin-complex was 1% fetal calf serum (FCS) in 0.1M TRIS buffer at pH 7.6. For then removed and chilled on ice for at least 30 minutes before being applied to tissue sections. The incubation steps leading to the generation of the antibody complex probes are summarized in Table 2.

TABLE 2

PREPARATION OF ANTIBODY COMPLEXES IN VITRO

1. Mix one volume of primary antibody with one volume of biotinylated secondary antibody.
2. Incubate the mixture at 37° C. for 1 hour.
3. Add one volume of diluted preimmune normal mouse serum to the mixture to achieve a final dilution of 1:2400. Mix thoroughly.

TABLE 2-continued

PREPARATION OF ANTIBODY COMPLEXES IN VITRO

4. Incubate the mixture at 37° C. for 1 hour.
5. Chill the mixture on ice for at least 30 minutes before application to tissue sections.

Immunostaining Using Antibody Complexes As Antigen-Specific Probes

The subsequent application of the antibody complexes to tissue sections utilized procedures similar to those required for the standard ABC method. Briefly, the tissue sections were deparaffinized in xylene and rehydrated in graded alcohols. Following treatment with 5% $H_2O_2$ in methanol for 30 minutes, the slides were washed in running tap water for 10 minutes, immersed in 0.1M TRIS buffer at pH 7.6 for 5 minutes, and then blocked in 5% non-fat dried milk plus 1% FCS in 0.1M TRIS buffer for 1 hour at room temperature. The tissue sections were then washed in 2 changes of 0.1 TRIS buffer, 3 minutes each, and immersed in 2% FCS in 0.1 TRIS buffer (FCS-TRIS) for at least 10 minutes at 4° C. Each tissue section was overlaid with approximately 90–100 μl of the antibody complex solution and incubated at 4° C. in a pre-chilled moist chamber for 12–18 hours. This incubation step was terminated by two 10 minute washes in 0.1M TRIS buffer at room temperature. All of the subsequent steps were also performed at room temperature. After a 10 minute wash in FCS-TRIS, the sections were covered with horseradish peroxidase (HRP) labelled streptavidin-biotin-complexes (BioGenex) diluted to the same extent as the secondary antibody which was within the recommended range of dilution of the vendor (i.e., 1:10 to 1:100). Excess streptavidin-biotin-complexes were washed away after a 30 minute incubation by 2 changes of 0.1M TRIS buffer for 5 minutes each. The bound HRP was visualized by treating the slides for 10 minutes with freshly prepared and filtered 0.05 mg/ml diaminobenzidine tetrahydrochloride (DAB) (Sigma) in 0.1M TRIS buffer containing 0.01% Triton X-100 (Sigma) and 0.01M imidazole and 0.03% $H_2O_2$ (28). Finally, the slides were counter-stained with Gill's hematoxylin, dehydrated, cleared and coverslipped.

Standard Staining Method

For comparison, a standard ABC method was used that was based on the protocol described by Hsu et al. supra. When the slides were incubated with the streptavidin-biotin-complex, this and subsequent steps in the standard and modified ABC method were the same. Indeed, at this point, slides probed with the modified or standard ABC method were developed together in the same DAB solutions to visualize bound HRP.

The supernatant from the $SP_2/O-Ag14$ mouse myeloma cell line (a non-secreting cell line) was used as negative control. Positive controls included sections of postmortem human cerebellum that were fixed and processed as the mouse tissues. These sections were immunostained in parallel with the sections of mouse tissues. Further, 2 different mAbs with different antigen specificities were applied to sections in the same experiment as positive controls for each other, and the modified and standard ABC procedures were conducted in parallel.

Using a modified ABC staining technique, a significant reduction in background staining due to endogenous immunoglobulin was demonstrated, as well as crisp antigen specific staining using a variety of mouse and rat mAbs. Despite a slightly decreased staining with certain mAbs, the invention produced strong positive antigen specific staining with all the mAbs used here. Since vascular structures may be defective in some tumor tissues, and leaky vessels with structural defects have been demonstrated in brain tissues surrounding tumors, endogenous immunoglobulin may accumulate in these areas. This is a source of confounding background staining using conventional indirect immunohistochemical methods. Thus, this method is useful for the studies of normal or diseased mouse tissues which otherwise would exhibit high background staining due to endogenous immunoglobulins.

The important step in the method of the invention is the use of complexes formed by the primary mAbs and a secondary antibody in vitro. Thus, the formation of "stainable" molecular complexes by the primary mAbs, the secondary antibodies and the normal mouse immunoglobulin is of paramount importance. Although several different mAbs formed complexes that were effective antigen specific probes, poorly understood factors may hinder the sensitivity of this method. For example, the complexes may cause stearic hindrance and make the antibody antigen binding kinetically unfavorable. Also, very large complexes may not bind avidly to tissue antigens. Further, some primary mAbs may bind weakly to the secondary antibody. In this case, abundant complexes formed by the secondary antibody and the immunoglobulin in the normal mouse serum may develop. Obviously, the latter complexes are not useful antigen specific probes. Finally, since our understanding of how an antibody interacts with its antigen is still limited (Wilson I. A., et al., "Structural Aspects of Antibodies and Antibody-Antigen Complexes," *Ciba Foundation Sym.*, 159:13 (1991), it is possible that when the secondary antibody complexes with the primary antibody, conformational changes may occur that modify the interaction of the primary antibody with the antigen.

If a reduction in antigen binding by the primary antibody in a complex results from stearic hindrance and inappropriate complex formation, further refinements of the method could overcome these limitations. For example, the conventional biotinylated secondary antibody could be replaced with biotinylated Fab' fragments that recognize the primary mAbs to reduce stearic hindrance and preclude the formation of complexes comprised only of secondary antibodies and normal mouse immunoglobulins.

The staining technique of the present invention represents an economic and convenient way to study normal and diseased tissues with mAbs. This method is especially useful when perfusion alone is insufficient to eliminate endogenous immunoglobulins. The present invention is likely to facilitate efforts to use transgenic mice as model human diseases.

The invention is further illustrated by means of the following, non-limiting examples.

EXAMPLES

Example 1

Tissues And Xenografts Processing

Normal young adult Balb/C mice were purchased from Charles River Laboratory (Cambridge, MA). The transgenic mice from Tg(PNMT, SV40E)Bri59 line carrying a human phenylethanolamine N-methyltransferase SV40 early fusion gene has been described earlier (Baetge et al., supra; Hammang J. P., et al., "Immortalized Retinal Neurons Derived from SV40 T-Antigen-Induced Tumors in Transgenic Mice," *Neuron*, 4:775 (1990)). Spontaneous bilateral primitive cellular tumors resembling retinoblastoma and bilateral pheochromocytomas develop postnatally in these mice. The morphological features and biological properties of these transgenic tumors have been reported previously.

For tumor transplantation studies, nude mice (NCrNu homozygous) were purchased from the National Cancer Institute, Fedrick Cancer Center, Bethesda, MD. The xenografts were made as described previously (Friedman H. S., et al., "Establishment and Characterization of Human Medulloblastoma Cell Line and Transplantable Xenograft D283," *Med. J. Neuropathol. Exp. Neurol.*, 44:592 (1985)). Briefly, about 5 x 10 D283 MED-NGFR cells were injected stereotaxically into the brains of anesthetized nude mice. As described elsewhere and incorporated herein by reference, (Friedman et al., supra; Pleasure S. J., et al., "Introduction of Nerve Growth Factor (NGF) Receptors into a Medulloblastoma Cell Line Results in Expression of High- and Low-Affinity NGF Receptors but not NGF-Mediated Differentiation," *Proc. Natl. Acad. Sci., USA*, 87:8496 (1990)), these cells are a human medulloblastoma cell line. They exhibit an immature neuronal phenotype and they are genetically engineered to express the human nerve growth factor receptor (NGFR). These mice were sacrificed three weeks after xenograft injection.

All of the mice were deeply anesthetized by intraperitoneal injection of Ketamine (83.3 mg/Kg) and Xylazine (16.6 mg/Kg) prior to sacrifice at which time they were perfused with 30 ml of 0.1M TRIS buffer (Sigma Chemical Co., St. Louis, Mo.) at pH 7.6 followed by 50 ml of 150 mM NaCl in 70% ethanol by a perfusion pump (model BSP, Braintree Scientific Inc., Braintree, Mass.) set at a rate of 217 ml/hr. The brain, both eyes, and both adrenal glands were dissected out and immersed in the same fixative for 24 to 48 hours at room temperature. They were infiltrated by paraffin in a Shandon Hypercenter (Shandon, Pittsburgh, Pa.) and embedded into paraffin blocks. To assess the modified ABC method in tissues form other species, samples of normal human postmortem cerebellum from a 53 year old neurologically normal subject were immersion fixed in the same fixative, embedded in the same manner and used in these studies.

Paraffin sections were cut 5 μm thick and affixed to poly-L-lysine coated glass slides by incubating them in an oven at 37° C. for 1 hour. These preparations were stored at room temperature for 1-2 weeks prior to immunohistochemical analysis.

Example 2

Primary Antibodies

The mAbs used here as primary antibodies and the working dilutions or concentrations at which they were employed are summarized in Table 1. All of the primary mAbs used in this study were raised in mouse or rat. SY38, an anti-synaptophysin mAb and NR4, a mAb raised to the low molecular weight neurofilament (NF) subunit (NF—L) were purchased from Boehringer Mannheim (Indianapolis, Ind.). HO14, DP1, RMd020, RM055, and RM093 recognize defined epitopes in either the medium (NF—M) or high molecular weight (NF—H) NF subunits. The phosphorylation state of the NF proteins (i.e., independent; non-phosphorylated; poorly (+), moderately (++) and heavily (+++) phosphorylated) containing the epitopes recognized by these mAbs have been defined as described by Lee et al. (Lee V. M.-Y., et al., "Monoclonal Antibodies Distinguish Several Differentially-Phosphorylated States of the two Largest Rat Neurofilament Subunits (NF—H and NF—M) and Demonstrate their Existence in the Normal Nervous System of Adult Rats," *J. Neurosci.*, 7:3474 (1987)). Monoclonal antibody 2.2B10 (Lee V. M.-Y., et al., "Monoclonal Antibodies to Gel-Exised Glial Filament Protein and their Reactivities with other Intermediate Filament Proteins," J. Neurochem., 42:25 (1984)) is a mAb specific for glial fibrillary acidic protein (GFAP) and the anti-MBP mAb, recognizes myelin basic protein (MBP). A mAb, MOC-1 (Molenaar W. M., et al., "Neuroectodermal Tumors of the Peripheral and the Central Nervous System Share Neuroendocrine, N-CAM-Related, Antigens with Small Cell Lung Carcinomas," *Acta. Neuropathologica*, 83:46 (1991); Moolenaar CECK, et al., "Expression of Neural Cell Adhesion Molecule-Related Sialoglycoprotein in Small Cell Lung Cancer and Neuroblastoma Cell Lines H69 and CHP-212," *Cancer Res.*, 50:1102 (1990)), has been shown to recognize a human neural cell adhesion molecule (N—CAM). FNP7 is a recently developed mAb raised to a non-phosphorylated synthetic peptide corresponding to the amino acid sequence of rat NF—M EEKGKSPVPKSPVEEKG (SEQ ID NO: 1) in Balb/C mice. This sequence is part of the peripheral domain in rat NF—M. Four of the mAbs, DP1, HO14, 2.2B10, and anti-MBP are rat mAbs, the others are mouse mAbs.

Example 3

Antibody Purification And Quantitation

Both FNP7 and RM093 were purified by ammonium sulfate precipitation followed by high performance liquid chromatography (HPLC). Briefly, ascites fluid was harvested from mice bearing the peritoneal hybridomas. A saturated ammonium sulfate solution (pH 7.4) was added to the ascitic fluid to achieve a 40% concentration. The mixture was stirred at 4° C. for 2 hours, centrifuged at 10,000 rpm for 10 minutes and the pellets were resuspended in 2 times the original volume of phosphate buffer saline (PBS) pH 7.4 before dialysis against 4 L of 20 mM TRIS buffer at pH 8.5 at 4° C. overnight.

A DEAE-5PW column (Millipore Corporation, Milford, Mass.) with a maximum protein loading capacity of 3.75 g/column connected to an HPLC (WATERS system, Millipore Corporation) was equilibrated with 20 mM TRIS buffer at pH 8.5. About 125 mg of antibody extract were loaded in the column and washed with 20 mM TRIS buffer at pH 8.5 for 5 minutes followed by elution using a sodium chloride solution gradient (up to 300 mM) over a 60 minute period. Fractions containing the antibody were identified by SDS-PAGE and their specificities against the antigens were determined by immunoblotting.

The protein concentrations of different mAbs were quantitated with the Coomassie Blue G250 reagent (Pierce, Rockford, Ill.) using bovine serum albumin (Pierce) as standard.

at 405 nm by a spectrophotometer (Titertek Multiscan, Flow Laboratories, Va.).

| Page: 1 | | Raw Sequence Listing<br>Patent Application US/07/915,919<br>SEQUENCE LISTING | 07/30/92<br>23:16:23 |
|---|---|---|---|
| | 1 | | |
| | 2 | | |
| | 3 | (1) GENERAL INFORMATION: | |
| | 4 | (i) APPLICANT: Trojanowski and Lee | |
| | 5 | | |
| | 6 | (ii) TITLE OF INVENTION: Modified Avidin-Biotin Technique | |
| | 7 | | |
| | 8 | (iii) NUMBER OF SEQUENCES: 1 | |
| | 9 | (iv) CORRESPONDENSE ADDRESS: | |
| | 10 | (A) ADDRESSEE: Woodcock Washburn | |
| | 11 | Kurtz Mackiewica & Norris | |
| | 12 | (B) STREET: One Liberty Place - 46th Floor | |
| | 13 | (C) CITY: Philadelphia | |
| | 14 | (D) STATE: PA | |
| | 15 | (E) COUNTRY: USA | |
| | 16 | (F) ZIP: 19103 | |
| | 17 | (v) COMPUTER READABLE FORM: | |
| | 18 | (A) MEDIUM TYPE: DISKETTE, 3.5 INCH, 1.44 Mb STORAGE | |
| | 19 | (B) COMPUTER: IBM PS/2 | |
| | 20 | (C) OPERATING SYSTEM: PC-DOS | |
| | 21 | (D) SOFTWARE: WORDPERFECT 5.1 | |
| | 22 | (vi) CURRENT APPLICATION DATA: | |
| | 23 | (A) APPLICATION NUMBER: n/a | |
| | 24 | (B) FILING DATE: Herewith | |
| | 25 | (C) CLASSIFICATION: | |
| | 26 | (vii) PRIOR APPLICATION DATA: | |
| | 27 | (A) APPLICATION NUMBER: | |
| | 28 | (B) FILING DATE: | |
| | 29 | (viii) ATTORNEY/AGENT INFORMATION: | |
| | 30 | (A) NAME: Jane Massey Licata | |
| | 31 | (B) REGISTRATION NUMBER: 32,257 | |
| | 32 | (C) REFERENCE/DOCKET NUMBER: UPN-1066 | |
| | 33 | (ix) TELECOMMUNICATION INFORMATION: | |
| | 34 | (A) TELEPHONE: (215) 568-3100 | |
| | 35 | (B) TELEFAX: (215) 568-3439 | |
| | 36 | (2) INFORMATION FOR SEQ ID NO: 1: | |
| | 37 | SEQUENCE CHARACTERISTICS: | |
| | 38 | (A) LENGTH: 17 | |
| | 39 | (B) TYPE: amino acid | |
| | 40 | (D) TOPOLOGY: linear | |
| | 41 | (xi) SEQUENCE DESCRIPTION: SEQ ID NO: 1: | |
| | 42 | Glu Glu Lys Gly Lys Ser Pro Val Pro Lys Ser Pro Val Glu Glu | |
| | 43 | 1    5    10    15 | |
| | 44 | | |
| | 45 | Lys Gly | |
| | 46 | | |

| PAGE: 1 | | SEQUENCE VERIFICATION REPORT<br>PATENT APPLICATION US/07/915,919 | DATE: 07/30/92<br>TIME: 23:16:25 |
|---|---|---|---|
| LINE | ERROR | ORIGINAL TEXT | |
| 23 | Wrong application Serial Number | (A) APPLICATION NUMBER: | |

| PAGE: 1 | SEQUENCE MISSING ITEM REPORT<br>PATENT APPLICATION US/07/915,919<br>MANDATORY IDENTIFIER THAT WAS NOT FOUND<br>STRANDEDNESS | DATE: 07/30/92<br>TIME: 23:16:25 |
|---|---|---|

| PAGE: 1 | | SEQUENCE CORRECTION REPORT<br>PATENT APPLICATION US/07/915,919 | DATE: 07/30/92<br>TIME: 23:16:25 |
|---|---|---|---|
| LINE | ORIGINAL TEXT | CORRECTED TEXT | |

Example 4

Antibody Isotype Determination

Isotyping was performed by ELISA using NF proteins as antigens coated to the ELISA plates followed by incubation with the mAbs, or by directly coating of the mAbs on the ELISA plate without antigen. The mAbs were then detected by isotype specific peroxidase labeled antibodies (Southern Biotechnology, Birmingham, Ala.). The reaction was visualized in a solution containing 0.3 mg/ml 2,2'-azino-bis(3-ethylbenzthiazoline-6-sulfonic acid) (ABTS) and 0.03% $H_2O_2$ in 0.1M citrate buffer at pH 4.5. The reaction was quenched by 10% SDS solution and optical densities were measured

What is claimed is:

1. A method for preparing an antigen specific complex comprising incubating a selected primary antigen specific monoclonal antibody which is not bound to said primary antigen with a selected biotinylated secondary antibody to produce a complex of the primary and secondary antibodies.

2. The method of claim 1 wherein said incubating step comprises incubating a selected volume of the primary antibody with an equal volume of the secondary antibody and subsequently adding diluted normal mouse serum to achieve a final concentration of about 1:1200 to about 1:3200.

3. The method of claim 2 wherein the incubating step is performed at a temperature of from about 35° C. to about 39° C. for up to 60 minutes.

4. The method of claim 2 wherein the incubating step is performed at 37° C. for one hour.

5. The method of claim 2 wherein the selected volume is from about 0.5 ml to about 3.0 ml.

6. The method of claim 2 wherein the diluent for the primary antibody-biotinylated secondary antibody complex is 1% fetal calf serum in 0.1M TRIS buffer at pH 7.6.

7. The method of claim 2 further comprising chilling the complex of the primary and secondary antibodies at about 2° C. to about 6° C. for at least 30 minutes before it is applied to tissue sections.

8. The method of claim 1 wherein the selected secondary antibody is selected from the group consisting of biotinylated anti-mouse, biotinylated anti-rat or biotinylated anti-rabbit antibodies.

* * * * *